United States Patent [19]

Durda et al.

[11] Patent Number: 4,814,275

[45] Date of Patent: Mar. 21, 1989

[54] MONOCLONAL HYBRIDOMA ANTIBODY SPECIFIC FOR A HUMAN EPITHELIAL ANTIGEN

[75] Inventors: Paul J. Durda, Needham, Mass.; David J. Green, Wilmington, Del.; Marcia J. Stone, Wellesley; Dennis E. Vaccaro, Wellesley, both of Mass.

[73] Assignee: E.I. DuPont de Nemours and Company, Wilmington, Del.

[21] Appl. No.: 733,065

[22] Filed: May 13, 1985

[51] Int. Cl.$^4$ .................. C07K 15/04; A61K 39/395; C12N 5/00; G01N 33/535

[52] U.S. Cl. .................. 435/240.27; 424/1.1; 424/85.8; 530/387; 436/513; 436/518; 436/536; 436/537; 436/542; 436/548; 435/7; 435/68; 435/172.2; 935/104; 935/106; 935/108; 935/110

[58] Field of Search .................. 435/240, 241, 948, 68, 435/70, 172.2, 7, 29, 30; 530/387, 388; 436/518, 513, 536, 537, 542, 548; 424/1.1, 85; 935/95, 104, 106–108, 110

[56] References Cited

U.S. PATENT DOCUMENTS

| | | | |
|---|---|---|---|
| 4,172,124 | 10/1979 | Koprowski et al. | 424/85 |
| 4,196,265 | 4/1980 | Koprowski et al. | 435/2 |
| 4,349,528 | 9/1982 | Koprowski et al. | 424/1 |
| 4,350,683 | 9/1982 | Galfre et al. | 424/85 |
| 4,522,918 | 6/1985 | Schlom | 435/68 |
| 4,562,160 | 12/1985 | Real | 436/539 |
| 4,571,382 | 2/1986 | Adachi | 435/7 |
| 4,584,268 | 4/1986 | Ceriani | 435/7 |
| 4,612,282 | 9/1986 | Schlom | 435/68 |
| 4,628,032 | 12/1986 | White | 435/240 |
| 4,642,291 | 2/1987 | Cairncross | 435/240 |
| 4,643,971 | 2/1987 | Fradet | 435/240 |

OTHER PUBLICATIONS

Bremer, E. G. et al., J. Biol. Chem., 259(23):14773–7 (1984) cited in Chem. Abstract CA 101 (25): 278201f.
Burchell, J. et al., J. Immunol. 131(1): 508–513 (1983) cited in Biosis Abstract 84:235918.
Cerian, R. L. et al., Somatic Cell Genetics 9(4):415–428 (1983) cited in Biosis Abstract 84:198368.
Buckman, R. et al., Lancet(2) 8313:1428–1430 (1982) cited in Biosis Abstract 83:270153.
Fredman et al., J. Biol. Chem. 258, pp. 11206 to 11210, 1983.
Anger et al., Hydridoma 1, pp. 139 to 147, 1982.
*Nature,* 256:495–497 (1975), Kohler and Milstein.
*Nature,* 266:550–552 (1977), Galfre et al.
*Eur. J. Immunol.,* 6:511–519 (1976), Kohler and Milstein.
*Handbook of Experimental Immunology,* (Blackwell Scientific, London, 1979) pp. 25.1–25.7, Weir (ed.).
*J. Immunol.,* 123(4):1548–1550 (1979), Kearney et al.
*Proc. Natl. Acad. Sci. USA,* 76(3):1438–1442 (1979), Herlyn et al.
*Proc. Natl. Acad. Sci. USA,* 78(5):3199–3203 (1981), Colcher et al.
*Proc. Natl. Acad. Sci. USA,* 78(8):5122–5126 (1981), Ueda et al.
*Proc. Natl. Acad. Sci. USA,* 78(7):4591–4595 (1981), Cuttitta et al.
*Canc. Res.,* 42:150–154 (1982), Mazauric et al.
*Canc. Res.,* 43:1301–1305 (1983), Canevari et al.
*Canc. Res.,* 43:1295–1300 (1983), Menard et al.
*In Vitro,* 17:1058–1070 (1981), Minna et al.
*Nature,* 266:495 (1977), Welsh.

Primary Examiner—Margaret Moskowitz
Attorney, Agent, or Firm—James A. Costello

[57] ABSTRACT

A monoclonal hybridoma antibody with specificity for an antigen that is present on tumors of epithelial origin; the cell line secreting said antibodies; a process for selecting the cell line; a diagnostic process for detecting the antigen and a therapeutic process for neutrailization of the angtigen.

4 Claims, No Drawings

MONOCLONAL HYBRIDOMA ANTIBODY SPECIFIC FOR A HUMAN EPITHELIAL ANTIGEN

BACKGROUND OF THE INVENTION

1. Field Of The Invention

This invention concerns a murine monoclonal antibody that recognizes an antigen present on tumors of epithelial origin. This invention also concerns the recognized antigen, in purified form, that reacts with the disclosed antibody. Also of concern are: the cell line that secretes the antibody, radiolabeled antibody, and diagnostic and therapeutic processes that employ the antibody.

2. State Of The Art

Fused cell hybrids of spleen cells and myeloma cells have been described in the literature by Kohler et al. in Nature, Vol. 256, 495 to 497 (1975) and in Eur. J. Immunol. Vol. 6, 511 to 519 (1976); by Milstein et al. in Nature, Vol. 266, 550 to 552 (1977); and by Walsh, Nature, Vol. 266, 495 (1977).

The techinque is also set out in some detail by Herzenberg and Milstein, in Handbook of Experimental Immunology, ed. Weir (Blackwell Scientific, London), 1979, pages 25.1 to 25.7. Relative to the parent myeloma cell line employed herein for the fusion event, see Kearney et al. J. Immunol., 123, 1548 to 1550 (1979).

Patents relating to antibodies against human tumors produced by hybrodoma technology include U.S. Pat. Nos. 4,172,124 and 4,196,265. Representative of the art concerning monoclonal antibodies that have specificity for antigens on carcinoma cells are U.S. Pat. No. 4,349,528 and U.S. Pat. No. 4,350,683.

Related publications include the following: Herlyn et al., Proc. Natl. Acad. Sci. USA 76, 1438 to 1442 (1979); Mazauric et al., Canc. Res. 42, 150 to 154 (1982); Canevari et al., Canc. Res. 43, 1301 to 1305 (1983); Colcher et al., Proc. Natl. Acad. Sci. USA 78, 3199 to 3203 (1981); Ueda et al., Proc. Natl. Acad, Sci. USA 78, 5122 to 5126 (1981); Cuttitta et al., Proc. Natl., Acad. Sci. USA 78, 4591 to 4595 (1981); Minna et al., In Vitro 17, 1058 to 1070 (1981). Finally, Menard et al., in Canc. Res. 43, 1295 to 1300 (1983) describe (MBrl) antibodies that react with apocrine sweat glands, not eccrine sweat glands, the antibodies recognizing an antigen which is a lipid.

The immune response to entry of a foreign substance into the body consists of secretion by plasma cells of "antibodies" which are immunoglobulin (Ig) molecules with combining sites that recognize particular determinants on the surface of the foreign substance, or antigen, and bind to them. Usually, the antibody (Ab) response to an antigen (Ag) is heterogeneous. Upon injection of a body with an immunogen, the body manfactures large numbers of antibodies directed against various components of the antigen and even against various determinant sites on the antigen. It is difficult to separate various antibodies and so conventional antisera contain mixtures of antibodies. It has long been a goal to design a source of antibodies that recognize and combine with specific antigen determinants.

One aspect of hybridoma technology concerns the fusion of myeloma cells with lymphocytes from animals which have been immunized with a particular antigen. Hybridomas manufacture monoclonal antibodies that are specific for a single antigenic determinant. Monoclonal antibodies are beginning to replace conventional antisera in standard diagnostic kits for such procedures as the radioimmunoassay. Significant work is also being done to adapt hybrodoma technology for therapeutic purposes.

Some properties that flow from an ideal parent cell line are (1) high fusion frequency; (2) high cloning efficiency; (3) the ability to grow rapidly in a serum medium; (4) no secretion of myeloma immumoglobulin (Ig) (5) stable production of large amounts of Ig after fusion; and (6) ability to grow when reinserted into the originating species. Immunoglobulin is the generic name for various isotypes of antibodies that include IgG, IgM, IgA, IgE, and the like. The various species of Ig have similarities and differences.

For example, all immunoglobulin molecules have a constant portion, that is highly conserved (i.e., constant) in amino acid sequence within a particular Ig subclass (e.g., $IgG_1$). This constant region is responsible for various biological effector functions (e.g., complement activation). The portion of the immunoglobulin molecule responsible for immunological specificity (i.e., specific antigen binding) is called the variable region. It is made up of the variable regions of the Ig heavy and light chains. These variable regions differ in amino acid sequence according to the antigenic determinant which the Ig recognizes.

A typical procedure for making hybridomas is as follows: (a) immunize mice with a certain immunogen; (b) remove the spleens from the immunized mice and make a spleen suspension in an appropriate medium; (c) fuse the suspended spleen cells with mouse myeloma cells from a suitable cell line; (d) dilute and cultue in separate containers the mixture of unfused spleen cells, unfused myeloma cells and fused cells in a selective medium which will not support the unfused myeloma cells, for a time sufficient to allow death of all the unfused cells; (e) evaluate the supernatant in each container containing a hybridoma for the presence of antibody to the immunogen; and (f) select and clone hybridomas producing the desired antibodies. Once the desired hybridoma has been selected and cloned, the resultant antibody is produced by in vitro culturing of the desired hybrodoma in a suitable medium. In an alternative method, the desired hybridoma can be injected directly into mice intraperitoneally to produce an ascites.

SUMMARY OF THE INVENTION

This invention concerns a novel monoclonal hybridoma antibody specific for a human epithelial antigen and the cell line secreting said antibody. The term "antibody" employed herein represents the described immunologically active antibody including any active fragment(s) derived therefrom. The antibody, IBD12, is further characterized as follows:

(1) It is secreted by the IBD12 hybridoma cell line in tissue culture and was shown by conventional immunochemical techniques using appropriate antisera to be an IgMk;

(2) The major immunoglobulin present in the ascites fluid was shown by ouchterlony analysis to be an IgM;

(3) It is not absorbed by protein A conjugated to Sepharose when incubated in 0.1 M sodium phosphate buffer, pH 8.0;

(4) It has an elution profile from Sepharose 4B consistent with an IgM; furthermore, electrophoretic analysis of the IBD12 antibody purified on Sepharose 4B indicates that the protein is greater than 90% pure IgM and, upon reduction of the disulfide bonds, the $1 \times 10^6$ Dalton pentameric IgM yields the expected 75,000 Dalton mu heavy chains and 25,000 Dalton light chains;

(5) Binding characterisics to various methanol-fixed tumor cell lines as determined in an enzyme-linked immunosorbant assay (ELISA, described in Example) are presented in Table 1:

TABLE 1

| | Cell Line | Absorbance at 488 nm |
|---|---|---|
| Breast | MCF-7 | 1.35 |
| Cell | MDA-MB-231 | 0.45 |
| Lines | HBL-100 | 0.7 |
| | Hs0578T | 0.0 |
| | ZR-75-1 | 0.9 |
| | BT-20 | 1.9 |
| Normal | WI-38 | 0.0 |
| Fibroblast Cell Lines | HEL | 0.0 |
| Other | WiDr | 0.55 |
| Tumor | SW-13 | 0.0 |
| Cell | A549 | 0.15 |
| Lines | G-361 | 0.0 |

As Table 1 demonstrates, the IBD12 antibody is reactive with some but not all breast tumor lines, is not reactive with normal fibroblast lines and is reactive with other tumor cell lines including a colo-rectal cell line, WiDr;

(6) The antibody has also been found to be reactive with some lung cancer cell lines such as SHP-77, SW-1573, SkLuci 6 and SkLuci 13, but not with other lung cancer cell lines such as Calu 1, SkMES1, SW-1271 and 9812;

(7) It displays similar reactivities with live unfixed cells from the same cell lines presented in Table 1 indicating that the IBD12 antibody recognizes an antigen which is present on the cell surface.

(8) The reactivities of IBD12 with 6-micron thick sections derived from formalin-fixed, paraffin-imbedded patient tissue samples were determined by the immunoperoxidase staining technique described in detail in the Example.

This invention also concerns the antigen which is recognized by IBD12 and which serves as a characteristic marker of the tumors described herein. This antigen, hereafter abbreviated HEA, is further identified as follows:

(1) It is present on the surface of MCF-7 cells as determined using either (i) indirect immunofluorescence or (ii) ELISA employing live MCF-7 cells.

(2) It is also present on the surface of red cells being apparently in high density on O-type cells and in lesser density on A- and B-type cells. From its distribution on various red cell types, the antigen appears to be related to, or actually be, H antigen. The antibody has been found to agglutinate all O-type red cells but not red cells having the Bombay phenotype.

(3) It has an apparent molecular weight greater than about $4 \times 10^6$ Daltons when shed from MCF-7 cells. It appears not to be a glycolipid, because it is not extractable in appropriate chloroform/ethanol/water mixtures. It appears to contain carbohydrate evidenced by its immunological inactivation by periodate oxidation (1mM sodium periodate at pH 4.5, 23° C. for 60 min).

(4) The antigen does not appear to be a protein because (on methanol-fixed MCF-7 cells) it is not susceptible to proteoplytic digestion with the protease mixture, Pronase ®.

This invention also concerns radiolabeled or otherwise modified IBD12 antibodies; a diagnostic process for detecting presence of HEA; a therapeutic process for neutralizing the HEA with IBD12 antibodies or radiolabeled IBD12 antibodies; a method for making the hybridoma cell line, for radiolabeling or otherwise modifying the antibodies, and for purifying the antigen; and a method for selecting hybridoma cell lines secreting monoclonal antibodies that bind to cell surface-associated carbohydrate moieties. The latter method comprises surveying the cell population and selecting therefrom those that secrete monoclonal antibodies that inhibit the transfer of a sugar from a nucleotide-sugar to a carbohydrate moiety associated with a cell surface antigen and do not inhibit the activity of membrane-bound glycosyltransferase enzyme.

DETAILS OF THE INVENTION

One utility of the HEA is in the formulation of a standard against which to measure unknown HEA levels and in procedures to test the efficacy and correct dosages of IBD12. An in vitro diagnostic assay employs the IBD12 antibody to determine the presence and amounts of HEA antigen in the blood serum or plasma from patients. This assay uses immobilized IBD12 antibody to trap HEA antigen present in a sample. The amount of bound HEA is then determined by reacting it with labeled IBD12. Purified HEA from the MCF-7 cell line is used as a standard for quantitation.

This invention also concerns an in vitro method for diagnosing the presence of HEA in a patient comprising: (i) mixing a patient sample with a known amount of IBD12 monoclonal antibody, (ii) contacting the mixture of (i) with a known quantity of standard HEA, (iii) determining the concentration of HEA in the patient sample by difference between the amount of standard HEA that would have bound to the antibody if there were no HEA in the patient sample and the amount of standard HEA which actually did bind to the antibody.

This invention also concerns a method for the ex vivo determination of the presence of HEA in a subject comprising subjecting a tissue sample from the subject to an immunoperoxidase staining protocol and evaluating the tissue sample for a positive staining pattern.

A therapeutic method for treating a subject to neutralize the tumor that displays HEA comprises contacting the subject with IBD12. The IBD12 can be the appropriately tagged or untagged antibody itself, or a tagged immunological fragment thereof. By tagging is meant the chemical combination of a tumor-killing agent with the IBD12 antibody or antibody fragment. The tagging agent can be a radioisotope such as $^{131}$I or $^{67}$Cu; a toxin such as ricin; or diphtheria toxin. The $^{131}$I can be introduced covalently into antibody molecules via Chloramine T ®, lactoperoxidase or Iodogen ® dependent reactions. The $^{67}$Cu can be attached via an appropriate metal chelator which is bonded to the antibody. The biological toxins, ricin and diphtheria toxins, can be covalently conjugated to the IBD12 antibody via glutaraldehyde or carbodiimide.

IBD12 antibody has been radiolabeled with $^{125}$I using the method of Greenwood et al., *Biochem. J.*, 1963, 89:114, with some modifications. To 100ug of Ab was added 2.0mCi of carrier free Na $^{125}$I and 0.025 mg Chloramine-T ®. The mixture was gently mixed at room temp for 1 minute. The reaction was stopped by the addition of 0.050mg L-tyrosine. The iodinated Ab was then separated on a Sephadex G-25 column.

The radiolabeled IBD12 antibodies have been shown to react with fixed MCF-7 cells and not with normal fibroblast lines (i.e. the reactivity pattern is similar to that of the unmodified IBD12 antibody). Disruption of the IBD12 antibody molecule with 2-mercaptoethanol and SDS followed by SDS polyacrylamide gel electrophoresis to separate the peptide chains results in $^{125}$I being found in both the heavy and light chains.

This invention also concerns a method for substantially cleansing blood serum, or other material, of human epithelial tumor cells that have a cell surface antigen with an apparent molecular weight greater than about $4 \times 10^6$ Daltons and a chemical profile of the antigenic determinant consistent with the presence of carbohydrate, but not consistent with the presence of glycolipid and protein, the method comprising binding said cells to IBD12 in an affinity chromatography format and separating the material cleansed of the tumor cells from the tumor cell-IBD12 complexes.

This invention also concerns a method for making the described murine hybridoma cell line by fusing a mouse spleen cell produced in response to MCF-7 immunogen with a nonsecretor myeloma cell line P3×Ag8, variant 653.

This invention also concerns a method for making IBD12 antibody by secreting said antibody from the described murine hybridoma cell line.

This invention also concerns a method for tagging IBD12 antibody by contacting it with at least one or an $^{131}$I or $^{67}$CU isotope or a ricin or diphtheria toxin.

This invention also concerns a method for purifying HEA antigen comprising (1) contacting said antigen with an antibody that reacts with MCF-7, MDA-MB-231, HBL-100, ZR-75-1 and BT-20 breast tumor lines but not with Hs0578T breast tumor line, and forming an antigen-antibody complex, and (2) separating the antigen from the antibody.

This invention also concerns a diagnostic method for determining the amount of HEA antigen in a subject comprising (i) contacting IBD12 antibody in an immobilized form with blood serum or plasma from the subject, (ii) binding any HEA in said serum or plasma to the immobilized antibody, (iii) reacting the bound HEA with said antibody that has been radiolabeled, and (iv) determining the amount of bound HEA by comparison with one or more known concentrations of HEA 8751.

The following Examples illustrates the invention. The cell line secreting IBD12 has ATCC Accession No. HB 8751.

EXAMPLE

The general method used for production of antibody-secreting somatic cell hybrids was previously described by Gefter et al. in Somatic Cell Genetics 3, 321 (1977) and by Marshak-Rothstein et al. in Jour. Immunol. 122, 2491 (1979). Briefly, a Balb/c mouse was immunized intraperitoneally on day zero with MCF-7 (ATCC Accession No. HTB22) membranes (100 µg of protein) mixed 1:1 with complete Freunds adjuvant 0.2 mL total volume. The mouse was boosted on days 51 and 73 with the same amount of immunogen mixed 1:1 with incomplete Freunds adjuvant. On day 100 the mouse was boosted with 100 µg of immunogen mixed 1:1 with complete Freunds adjuvant.

Four days later, the spleen of the mouse was removed and fused with the non-secretor myeloma cells of cell line P3×Ag8, variant 653, ATCC Accession No. CRL 1580; see Kearney et al. Jour. Immunol. 123, 1548 to 1550 (1979). More particularly, after sacrifice of the mouse, spleen cell suspension was prepared in RPMI 1640 medium ($5 \times 10^7$ lymphocytes/ml). To 1 ml of spleen cells was added $5 \times 10^6$ myeloma cells, P3×Ag8, variant 653 in a round bottom plastic tube. This cell mixture was centrifuged at 700xg for five minutes at room temperature. After removal of the supernatant, the cells were suspended by tapping the tube and 0.5 ml of 37° C., 30% w/v polyethylene glycol 1000 (PEG) (Baker Chem. Co.) was added. The cells with PEG were immediately centrifuged at room temperature 700xg for 3.5 minutes. Ten minutes after the addition of PEG, the cells were gently resuspended and 4.0 ml of RPMI 1640 was added to the tube. This suspension was then poured into a 100 mm diameter Petri dish containing 4.5 ml of RPMI 1640 and 1.5 ml of horse serum. These cells were then incubated at 37° C. for 18 to 24 hours. The cells were then gently resuspended and diluted to 65 ml in RPMI 1640 containing 10% horse serum and hypoxanthine/aminopterin/thymidine (HAT; $10^{-6}$M: $8 \times 10^{-10}$M:$1.6 \times 10^{-7}$M, respectively).

Cells were than pipetted at two drops/well into 96 well microtiter plates (approximately $2 \times 10^5$ spleen cells/well). Approximately 14 days later, tissue culture supernates from wells containing colonies were tested for binding to MCF-7 cells by the following procedures. Procedure (1): An enzyme-linked immunosorbant assay (ELISA) procedure wherein MCF-7 cells were grown in 96 well polyvinyl chloride microtiter plates (CoStar Cat. No. 2596) until approximately confluent. The microtiter plates had been coated with 0.1% w/v poly-L-lysine (Sigma P-0879), m.w. 4000, and subjected to u.v. sterilization prior to being used for growing cells. These adherent cells were fixed by dipping the plate in 100% methanol followed by air drying. Hybridoma supernates were added to the wells containing fixed MCF-7 cells, and plates were incubated at 4° C. for 16 to 20 hours. Hybridoma supernates were then removed by aspiration and the wells were washed three times with PBS buffer containing 1% w/v serum albumin (PBSBSA).

Then, 100 µl of PBSBSA diluted anti-mouse IgG antibody conjugated to horse radish peroxidase (GAMHRP) (New England Nuclear Corp.) diluted 1:500 in PBSBSA was added to the wells, followed by incubation at 37° C. for one hour. GAMHRP was then removed by aspiration and the wells washed once with 100 µl of PBSBSA and twice with distilled water. Presence of bound GAMHRP was determined by adding to the wells 100 µl of the substrate of HRP, 0.2% w/v o-phenylenediamine in citrate-phosphate buffer (0.009M citric acid, 0.03M K$_2$HPO$_4$) containing 0.015% hydrogen peroxide. HRP in combination with its substrate resulted in a yellow colored product; development of the product was allowed to occur at room temperature for 10 to 20 minutes. The enzymatic reaction was terminated by the addition of 100 µl of 4.5M H$_2$SO$_4$. Measurement of the resultant reaction product was accomplished by determining optical density at 488 nm. Presence of yellow color in the wells indicated that antibody was present in the hybridoma supernatants which could bind to fixed MFC-7 cells and be recognized by the GAMHRP reagent.

Procedure (2): Hybridoma supernates were also added to the wells of microtiter plates made of soft plastic. The microtiter plates had been coated with BSA prior to use. Then, 100 µL of 20 mM tris maleate pH 6.8 and 10 μL of MCF-7 membranes (approximately 7 μg of protein/mL) were added to each well. The hybridoma supernates were incubated with the MCF-7 membranes for 1 to 1½ hours at 30° C. or overnight at 4° C. Then, either 10 μL of a mixture of 5 mM McCl$_2$ and CMP($^3$H)NANA (NEN Corp.) and 10 μL of desialylated fetuin (25 mg protein/mL) or 10 μL of a mixture of 5 mM McCl$_2$ and UDP($^3$H)Gal (NEN Corp). and 10 μL of desialylated, degalactosylated fetuin (25 mg protein/mL) was added to each well. Control plates containing tritiated nucleotide sugars, but not the fetuin, were also set up. Plates were incubated for 2 to 2½ hours at 37° C. Ice cold TCA was then added to each well. The plates were stored at 4° C. for 10 minutes, then centrifuged for 10 minutes. After aspiration the microtiter wells were cut out of the plates and the $^3$H-sugars were counted by conventional liquid scintillation counting procedures.

Cells in wells containing hybrids secreting an IgG that bound to MCF-7 cells as determined by Procedure (1), that inhibited the transfer of a sugar from a nucleotide-sugar to a carbohydrate moiety associated with MCF-7 membranes as determined by Procedure (2), and that did not inhibit the activity of a glycosyltransferase enzyme associated with the MCF-7 membranes as determined by Procedure (2) were expanded and subjected to limiting dilution cloning.

After limiting dilution cloning, ascites fluid containing the MCF-7 reactive antibody was produced in Balb/c mice as follows. Mice were primed with 0.5 mls of Pristane ® (Aldrich Chem. Co.) by intraperitoneal (i.p.) injection two weeks prior to i.p. innoculation with 1×10$^6$ cloned IBD12 hybridoma cells. After two to three weeks, the ascites fluid was removed with a syringe. Presence of MCF-7 reactive antibody was determined using Procedure (1) described above with various dilutions of the ascites fluid. Those samples showing the highest titer (1:10,000 to 1:50,000) were pooled and subjected to salting out with 50% ammonium sulfate at 4° C. Precipitate containing the IBD12 antibody was collected by centrifugation and dissolved in distilled water. This material was then subjected to gel filtration chromatography on Sepharose 4B ® (Pharmacia) and the peak containing reactivity for MCF-7 cells pooled to provide partially purified IBD12 antibody.

Immunoperoxidase Staining

To determine the reactivity of the IBD12 antibody with various tumor and tissue types, formalin-fixed paraffin-embedded tissue sections were employed. Staining techniques were carried out according to the following protocol:

(1) 10% formalin-fixed, paraffin-embedded, 6 micron sections were cut on a table top microtome. Sections were picked up on albumin coated slides and baked at 56° C. for two to three hours. (2) The sections were deparaffinized in 100% xylene for 30 minutes, then in 100% ethanol for 5 minutes. Endogenous peroxide was quenched by a 30 minute incubation with 0.6% hydrogen peroxide in 100% methanol. (3) The sections were rinsed in PBS and blocked with 10% normal goat serum in PBS containing 1% PBS (PBS:BSA). (4) The slides were wiped dry and 200 to 500 μl of antibody at 10 μg/ml in PBS:BSA were added over the tissue section. The sections were then incubated in a humidified chamber for 90 to 120 minutes at room temperature. Each tissue section sample was tested with a class-matched, IgM, and normal saline controls were run. (5) The tissue sections were washed extensively to PBS. This washing was carried out in separate staining trays to ensure that specific Ab samples were kept separate from the control slides.

(6) A secondary antiserum consisting of rabbit anti-mouse IgM (Miles Labs) was added to all tissue sections at a dilution of 1:100 in PBS:BSA. This was then incubated at room temperature in the humidified chamber for 30 minutes. (7) The sections were washed three times with PBS and subsequently incubated with goat anti-rabbit IgG:biotin at a dilution of 1:200 in PBS:BSA. The goat anti-rabbit IgG:biotin was part of an ABC Immunoperoxidase kit from Vector Laboratories. (8) The sections were washed three times with PBS and incubated with the avidin-biotin-horseradish peroxidase complex (part of the above ABC kit) diluted 1:100 in PBS:BSA. Incubation was at room temperature for 30 minutes. (9) Following five washings with PBS, diaminobenzidine at a concentration of 400 μg/ml in PBS was added to the sections. (10) After incubation for approximately 10 minutes, the sections were washed once with PBS and twice with distilled water. They were then counterstained in double strength Gill's hematoxylin (Lerner Labs) for two minutes; washed in water; dipped in 0.03 M acetic acid; washed in water again; developed in 0.01% ammonium hydroxide; washed in water; and finally dehydrated through 95% ethanol, 100% ethanol, and 100% xylene. Sections were then treated with Permount ® and coverslips were placed over the sections.

Test results of the reactivity of the IBD12 antibody at 4 to 10 μg/tissue section yielded strong staining of tumor cells in samples from patients with infiltrating ductal carcinoma of the breast. A reddish brown color was detected and was attributed to the presence of the reaction product of horseradish peroxidase which in turn is bound through various intermediates to mouse IgM antibody, IBD12. Hematoxyline which yields blue staining of nuclei was used as a counterstain to heighten the contrast with reddish-brown precipitates. The material staining wth the antibody appears to be (1) secreted, (2) attached to the cell surface and (3) also cytoplasmic.

The pattern of cytoplasmic staining is variable among different infiltrating ductal tumor samples. In some it is globular and supranuclear suggesting that the antigen is Golgi body-associated and destined for secretion. In others, the staining in pancytoplasmic, i.e., everywhere in the cytoplasm. That the antigen recognized is not tumor specific is indicated by the patchy staining of lobular units in tissue sections from patients with fibrocystic disease, a benign lesion. Note that when an IgM with specificity for an irrelevant antigen such as IgM specific for a mouse thymus antigen called Thy 1.2 is substituted for IBD12, no staining is observed.

Tumors that have shown positive staining with the IBD12 antibody include (1) lymphoid metastasis from infiltrating ductal carcinoma of the breast, (2) ovarian carcinoma, both endometrioid and papillary, (3) endometrial carcinoma, (4) adenocarcinoma of the lung, (5) transitional cell carcinoma of the bladder, (6) adenocarcinoma of the colon, (7) squamous cell carcinoma of the skin and of the tongue, (8) andeocarcinoma of the prostate and (9) papillary carcinoma of the thyroid. The staining patterns and intensities were variable. In some samples all tumor cells stained, e.g., some infiltrating ductal carcinomas of the breast; in others only a rare cell was stained, e.g., papillary carcinoma of the thyroid. The stained tumors are all of epithelial origin. Interestingly, no staining was observed of tumors of non-epithelial origin including melanoma, leiomyosarcoma, neuroblastoma, astrocytoma, and lymphoma. Bone marrow samples from a patient with a megaloblastic anemia and normal lymphocytes were also negative for antibody binding.

Mild staining of normal epithelial cells was sometimes observed, e.g. lobules from patients with fibrocystic breast lesions. Colonic epithelia from healthy individuals and from patients with non-neoplastic diseases were routinely found to be free of staining as were epithelial cells in adenomas without dysplasia. Occasionally, histologically normal tissue adjacent to the tumor was found to be stained. Tubular, villus, and tubularvillus adenomas with dysplasia all stained with the IBD12 antibody. Additionally, all colorectal adenocarcinomas of any grade (i.e., well to poorly differentiated) stained with the antibody.

The embodiments of the invention in which an exclusive property or privilege is claimed are defined as follows:

1. A murine hybridoma cell line that secretes IBD12 monoclonal antibody which binds to human epithelial cell surface H antigen.

2. A monoclonal antibody, IBD12, secreted by the hybridoma cell line according to claim 1.

3. A tagged monoclonal antibody according to claim 2, the tab being selected from the group consisting of isotope of I, isotope of Cu, ricin, and diphtheria toxin.

4. A tagged monoclonal antibody according to claim 3, wherein the tag is a radiolabel.

* * * * *